(12) United States Patent
Krook et al.

(10) Patent No.: US 8,733,362 B2
(45) Date of Patent: May 27, 2014

(54) ANTI-SNORE DEVICE

(76) Inventors: Ann-Christine Krook, Tyresö (SE);
Jonas Norberg, Tyresö (SE)

( * ) Notice: Subject to any disclaimer, the term of this patent is extended or adjusted under 35 U.S.C. 154(b) by 504 days.

(21) Appl. No.: 12/867,909

(22) PCT Filed: Dec. 12, 2008

(86) PCT No.: PCT/SE2008/000695
§ 371 (c)(1),
(2), (4) Date: Aug. 25, 2010

(87) PCT Pub. No.: WO2009/104996
PCT Pub. Date: Aug. 27, 2009

(65) Prior Publication Data
US 2010/0307512 A1    Dec. 9, 2010

(30) Foreign Application Priority Data

Feb. 18, 2008    (SE) ..................................... 0800364

(51) Int. Cl.
| A61F 5/24 | (2006.01) |
| A61F 5/56 | (2006.01) |
| A61F 13/00 | (2006.01) |
| A61F 5/37 | (2006.01) |
| A61F 5/00 | (2006.01) |

(52) U.S. Cl.
USPC .......... 128/848; 128/97.1; 128/845; 128/846; 602/5; 602/17; 602/18; 602/32; 602/902; 601/23; 601/39

(58) Field of Classification Search
CPC ............ A61F 5/00; A61F 5/04; A61F 5/042; A61F 5/048; A61F 5/05; A61F 5/05883; A61F 5/37; A61F 5/3707; A61F 5/56; A61F 13/12; A61H 2201/16; A61H 2201/1604; A61H 2201/1609; A61H 2201/1614
USPC ............... 128/97.1, 846, 848; 602/17–18, 32, 602/902, 5; 601/23, 39
See application file for complete search history.

(56) References Cited

U.S. PATENT DOCUMENTS

| 2,528,370 | A | | 10/1950 | Johnston |
| 4,366,815 | A | | 1/1983 | Broomes |
| 4,700,697 | A | | 10/1987 | Mundell et al. |
| 4,827,915 | A | * | 5/1989 | Gorsen ........................... 602/18 |
| 6,668,834 | B1 | | 12/2003 | Zikria |
| 7,549,968 | B2 | * | 6/2009 | Cojbasic ........................... 602/5 |
| 7,885,713 | B2 | * | 2/2011 | Campbell et al. ............... 607/48 |
| 2007/0256694 | A1 | | 11/2007 | Kussick |
| 2010/0036301 | A1 | * | 2/2010 | Baldauf et al. .................. 602/14 |

FOREIGN PATENT DOCUMENTS

| DE | 195 05 804 A1 | 8/1995 |
| GB | 2 226 239 A | 6/1990 |

* cited by examiner

*Primary Examiner* — Patricia Bianco
*Assistant Examiner* — Brandon L Jackson
(74) *Attorney, Agent, or Firm* — Dickstein Shapiro LLP

(57) ABSTRACT

A device for prevention of snoring in the form of a neck collar (1) with a middle section (2) for placement under the chin of a user, side sections (3, 4) connecting to said middle section and end parts (5, 6), optionally connectable to each other, consisting of a core of foam plastic contained in a covering. The foam plastic is a soft foam plastic, an opening (7) is formed in said middle section (2) and resilient means (14; 15; 27; 28) for adjustment of the height of the opening (7) and thereby the height of the middle section (2) are arranged in said opening (7).

9 Claims, 2 Drawing Sheets

ANTI-SNORE DEVICE

FIELD OF THE INVENTION

The present invention relates to a device for prevention of snoring, and more specifically to a device in the shape of a collar intended to be placed around the neck of a user and comprising a support for the chin of the user.

PRIOR ART

Snoring is a major problem for very many people, both indirect and direct. Snoring can eventually lead to sleep apnoea syndrome, which can lead to very serious consequences. Snoring leads to sleep deprivation, also for the one who snores. There are many different suggestions for solutions to this problem, everything from surgery in the throat to devices to be placed in the mouth, e.g. acrylic splints, or in the nose. There are also devices intended to raise the head and thereby keeping the airways open.

Thus e.g. DE 195 05 804 A1 describes a body, shaped like an orthopaedic collar exhibiting a support area for the lower jaw and two bulges intended to support the head behind the lower jaw. The body can preferably consist of a medium soft foam plastic. The intention is not only to keep the mouth shut but also to prevent the lower jaw from falling back. The foam plastic shall allow for the mouth to open without discomfort, to, for example, cough. A drawback of this neck collar is that it must be adjusted individually for a carrier to achieve optimal function, or the neck collar must be provided in lots of different sizes and heights, since large anatomic differences exist between different individuals. Another drawback is that the locking of the head and the jaw can be uncomfortable, even if the foam plastic is supposed to allow for a certain flexibility.

BRIEF DESCRIPTION OF THE INVENTION

An object of the present invention is to provide a device that prevents snoring by keeping the respiratory channels open at the same time as the drawbacks according to the prior art are reduced or completely eliminated.

Another object of the invention is to accomplish a device to prevent snoring, which is comfortable to use also in a sitting position, for example when travelling, when the risk that one will snore often is seen as something extremely embarrassing.

Yet another object of the invention is to achieve a device that prevents snoring, which allows for individual adjustment and thereby can be provided in only one or a few sizes, which can be adjusted to most individuals.

These and other objects are achieved by the present invention, whose characteristics are evident from the characterizing part of claim 1. Preferred and advantageous embodiments of the invention are specified in the subclaims.

BRIEF DESCRIPTION OF THE DRAWINGS

Additional advantages, characteristics and embodiments of the invention will be apparent from the following detailed description in connection with the appended drawings, in which.

DETAILED DESCRIPTION OF EMBODIMENTS OF THE INVENTION

Figure 1:
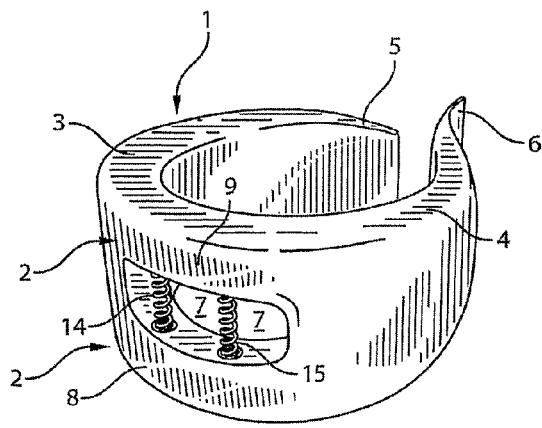
FIG. 1 shows the device according to the invention, in perspective, seen obliquely from the front.

In FIG. 1 the device is shown in a perspective view seen obliquely from the top, in the form of a neck collar 1 with a middle section 2, two side parts 3, 4 which end in free ends 5 and 6, respectively. An opening 7 is formed in the middle section of the neck collar.

The neck collar consists of a core of soft foam plastic surrounded by a suitable coating. With soft foam plastic is intended a foamed material which gives in to a light load, such as for instance the one occurring when the chin falls towards the chest when falling asleep. In the middle section of the device, which is intended to be placed under the chin of a user, the opening results in that the resistance towards compression from the material in the collar is further reduced.

Figure 2:
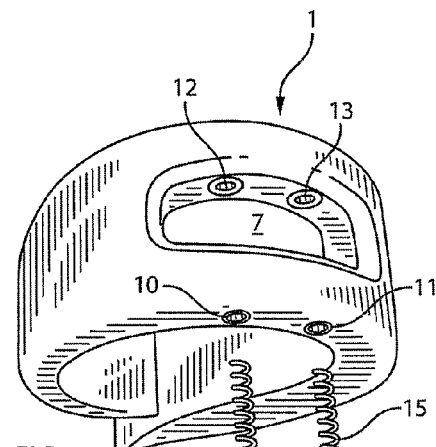
FIG. 2 shows a first embodiment of the device according to the invention in perspective, seen obliquely from underneath, partly dismounted.

In FIG. 2 the neck collar is shown in perspective seen obliquely from underneath. The opening 7 is confined by a lower part 8 and an upper part 9 of the middle section. In the lower part 8, bushings 10, 11 are arranged, extending through the entire lower part. In the upper part 9 are arranged support sleeves 12, 13, which open towards the inside of the opening. The bushings, support sleeves and two helical springs 14, 15, intended to be inserted in the bushings such is implied by the two arrows, together form a height adjustment means, whose function will be explained in detail below.

According to one embodiment of the invention, the bushings are formed with internal (female) thread, not shown on the drawing, which have the same pitch as the windings of the helical springs. Thereby a driving means 16, 17 can be arranged in the bushing end of each of the springs, by means of which the springs of the bushings can be rotated with a suitable tool twist. When the springs are rotated through the bushings and their free ends are lying in the supporting housings, the intention is that as an alternative, they shall be manually adjustable by rotating them between thumb and finger.

It is also possible to design the above mentioned conveyor means with a threaded outside so that these in cooperation with the internal thread in each bushing allow for adjustment by means of displacement of the spring upwards or downwards.

Figure 3:
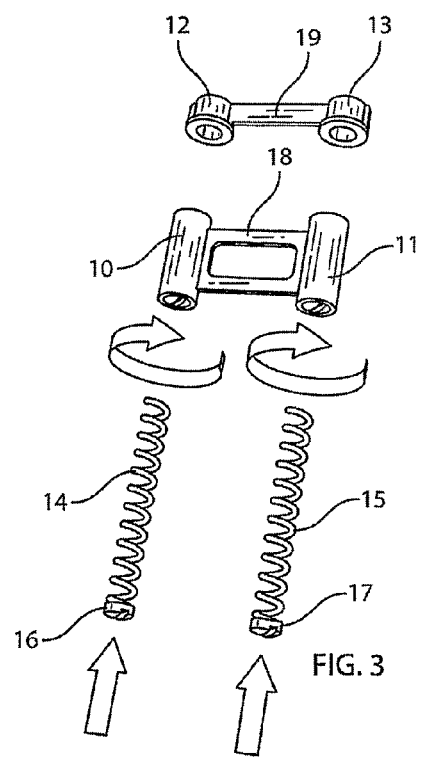
FIG. 3 shows an exploded view of a device for adjustment of the height of the device according to the invention.

In FIG. 3 is shown an exploded view of an embodiment of the height adjustment means. In the case with two helical springs, the bushings 10, 11 are preferably connected by rods 18 for locking of their internal position. In the manufacturing process the parts of the height adjustment means are connected with the surrounding foam material in a suitable manner, such as gluing/pasting, embedment or the equivalent so that it is surrounded or enclosed in the foam material, and possibly, because soft foam plastic is used, e.g. the wings can be arranged to further fixate the position of the device in the foam plastic. Likewise, the supporting housings 12, 13 are suitably also connected with rods 19, and the support sleeves can also be provided with protruding means such as wings to improve the positioning in the foam plastic, such as is further discussed below in connection with a second embodiment of the height adjustment means.

Before applying of the parts of the height adjustment device which shall be fastened in the foam plastic, the corresponding areas in the foam plastic is preferably cut to shapes equivalent to the parts of the height adjustment device to make sure that essentially no compression of the foam plastic will occur there.

Figure 5:
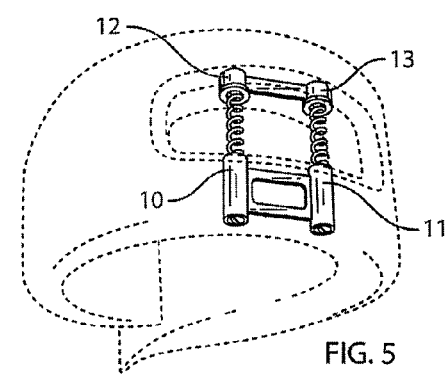
FIG. 5 shows the height adjustment device assembled in the device, shown with a dashed line, according to the invention.
Figure 4:
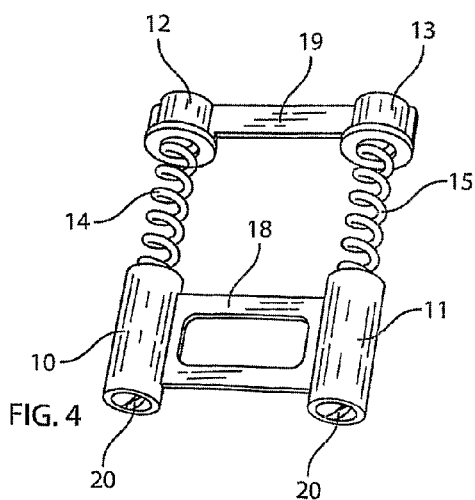
FIG. 4 shows the height adjustment device according to FIG. 3 in an assembled position.

In FIG. 4 the height adjustment device is shown in an assembled form, while it is shown assembled in the neck collar illustrated by a dashed line in FIG. 5.

When using the device according to the invention, the neck collar is placed around the neck, having the middle section provided with an opening, placed under the chin. The free ends 5, 6 can be connected to each other with Velcro® fastening or the like.

Advantageously, a covering can be arranged on the device according to the invention, which is to be removable and washable. Thereby, a Velcro® fastening or the equivalent can preferably be arranged on the covering to keep the two ends of the device together when used and prevent it from falling off during use.

The upper, towards the upper end confining part 9 of the neck collar is already, because of the soft foam plastic, very resilient, which is emphasized by the relative thinness compared to the side parts. With the springs the height of the neck collar's middle section can now be adjusted, according to the first embodiment by rotating the springs in the opening with the fingers, or alternatively, such as is also mentioned above, this rotation can take place with the aid of a tool, which is attached to the corresponding driver means, for example in the shape of a groove 20.

Figure 6:
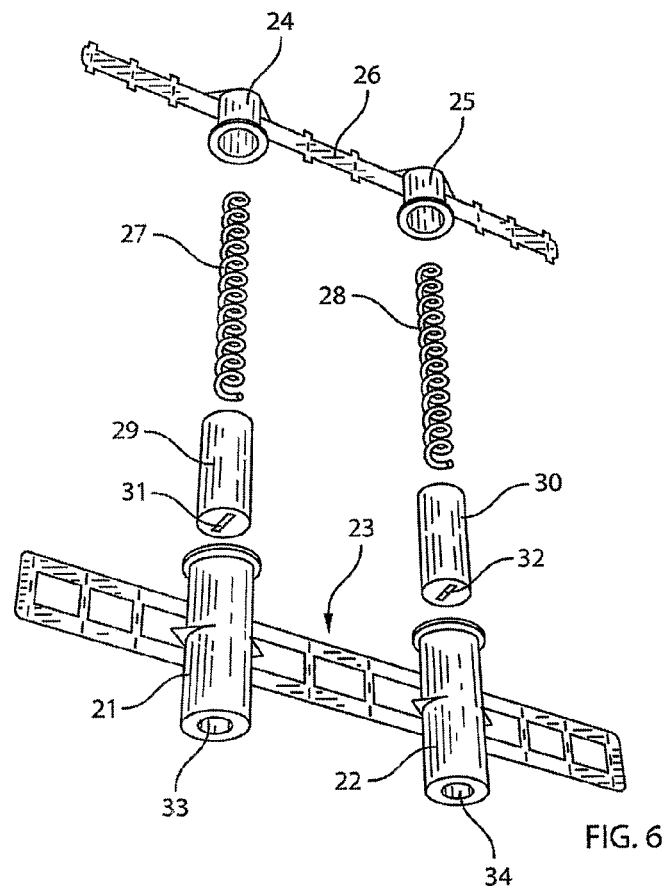
FIG. 6 shows a second embodiment of a device for adjustment of the height of the device, according to the invention.

In FIG. 6 is shown a second embodiment of the height adjustment means of the device according to the invention in an exploded view. Said means consist of two lower bushings 21, 22 connected by a rod 23 in the shape of a ladder, protruding from the bushings 21, 22 and thereby creating stability and durability for the attachment of the bushings in the foam plastic. The plastic material in the ladder 23 is supposed to be so soft that it does not considerably stiffen the device according to the invention.

Correspondingly, the support sleeves 24, 25 are connected with a plastic rail 26 protruding from the housings.

Two helical springs 27, 28 extend between the bushings 21, 22 and the support sleeves 24, 25 and work the same way as the springs according to the first embodiment. This embodiment differs from the first in that screw cups 29, 30 are arranged in the bushings 21, 22, which on their outside are threaded. On the inside of each bushing is arranged a tap or thread follower (not shown in the drawing), intended to run in each external thread on the screw cups. Underneath the screw cups is arranged conveyor means 31, 32 for example in the shape of a straight groove or a crossed groove. This is reached through the bottom of the bushings exhibiting an opening 33, 34, which optionally can have a diameter that is smaller than the external diameter of the screw cups, so that these not can be unscrewed from the device and be lost. Alternatively, said opening can have a diameter equivalent to, or just exceeding the diameter of the screw cups so that spring and screw cup can be assembled afterwards or replaced.

According to another embodiment not shown in the drawings, a stiff element can be arranged centrally in each spring, which will prevent the spring from breaking.

Figure 7:
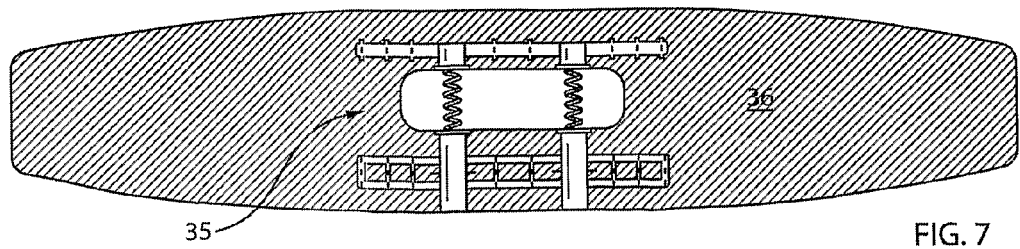
FIG. 7 shows the height adjustment device according to FIG. 6 assembled on a blank for the device according to the invention.

In FIG. 7 the height adjustment device 35 according to the second embodiment is shown applied on a blank 36 of the device according to the invention in the form of one half. The height adjustment device is applied between two such halves, preferably in correspondingly cut areas in the foam plastic with a form equivalent to the form of the height adjustment device and glued/pasted to the foam plastic at the same time as the foam plastic in each half is glued/pasted together or is in some other way connected to each other.

It is thus solely the springs that defines the height of the neck collar's middle section and also the resistance against compression.

The material of the spring shall have a stiffness chosen so that when a person is sleeping with relaxed muscles, the middle section of the neck collar upholds the chin, keeping the airways free. At the same time the mouth shall be able to open wide without any discomfort in the form of a great resistance, for example when coughing, yawning etc. Variation of the free length of the spring in the opening in the neck collar only gives an insignificant variation in the stiffness of the spring.

The invention has been described above in connection with a preferred embodiment. However, the invention is not limited exactly to the embodiments shown in the drawings, but to the contrary it is possible to switch the helical springs to other resilient means with adjustable height, such as springs of rigging screw type. It is also possible to replace the manual adjustment with a pneumatic, hydraulic or electric adjustment. The scope of the invention is defined by the appended claims.

The invention claimed is:

1. A device for prevention of snoring in the form of a neck collar having a middle section for placement under the chin of a user, side sections connecting to said middle section; and end parts optionally connectable to each other, said neck collar comprising a core of foam plastic contained in a covering, said foam plastic being a soft foam plastic, wherein said middle section comprises an opening in an area to be placed under the chin of a user with resilient height adjustment spring means arranged to be manually rotatably adjustable in order to adjust the height of said middle section to accommodate anatomic differences between users of the device, wherein the height adjustment spring means further comprises screw cups intended to be arranged in the bushings for taking up of one end of the helical spring, whereby the screw cups on their outside exhibit screw threads while at the same time that each bushing on their inside exhibits a tap or a thread follower, intended to interact with the threads of screw on the outside of the screw cups so that when screw cups are rotated with the driver means arranged on their underside, these can be moved upwards or downwards in relation to the bushing, whereby also the height of the opening in the device is adjusted.

2. The device according to claim 1, wherein said height adjustment spring means comprises at least one helical spring, at least one bushing arranged in a part of the device which delimits the opening downwardly and fastened thereto, as well as one support sleeve arranged in another part of the device delimiting said opening upwardly and fastened thereto for the taking up of the upper end of the spring.

3. The device according to claim 2, wherein said height adjustment spring means comprises two helical springs with adherent bushings or support sleeves for taking up of the springs.

4. The device according to claim 3, wherein the bushings are connected to each other with rods, whereby the internal position of the bushings are fixed.

5. The device according to claim 3, wherein the support sleeves are connected to each other with rods, whereby the internal positions of the support sleeves are fixed.

6. The device according to claim 2, wherein the bushing(s) and the support sleeve(s) are fastened in the foam plastic through gluing/pasting, embedment or the correspondent, whereby on each outside of the elements is arranged protruding elements of soft plastic material for further fixation in the foam.

7. The device according to claim 2, wherein the bushings exhibit an internal thread for screwing in or out of said spring, whereby the thread in the spring bushing is adapted to the pitch of the spring, whereby through manual rotation of the free spring in said opening, the height of the middle section or the opening can be adjusted.

8. The device according to claim 1, wherein said spring means are arranged in said opening in the foam plastic, and said height adjustment spring means is arranged to be manually adjustable through exposed portions of said spring means.

9. The device according to claim 1, wherein said height adjustment spring means is arranged to be adjustable through driver means accessible from underneath the device.

* * * * *